United States Patent [19]

Cain et al.

[11] Patent Number: 5,420,291

[45] Date of Patent: May 30, 1995

[54] **PROCESS IMPROVEMENT IN THE SYNTHESIS OF [R-(R*,R*)]-5-(3-CHLOROPHENYL)-3-[2-(3,4-DIHYDROXYPHENYL)-1-METHYLETHYL]-2-OXAZOLIDINONE**

[75] Inventors: William T. Cain, Nanuet; Kelvin Cruz, New Windsor; Kevin M. McCoy, Hoboken, all of N.Y.

[73] Assignee: American Cyanamid Company, Wayne, N.J.

[21] Appl. No.: 309,304

[22] Filed: Sep. 20, 1994

Related U.S. Application Data

[63] Continuation-in-part of Ser. No. 164,524, Dec. 9, 1993.

[51] Int. Cl.$^6$ .............................................. C07D 263/20
[52] U.S. Cl. ..................................................... 548/229
[58] Field of Search .......................... 548/229; 568/805

[56] References Cited

U.S. PATENT DOCUMENTS 5,061,727  10/1991  Bloom et al. .......................... 548/229
5,106,867   4/1992  Bloom et al. .......................... 514/376

*Primary Examiner*—Donald G. Daus
*Attorney, Agent, or Firm*—H. G. Jackson

[57] ABSTRACT

The invention is a process improvement for producing [R-(R*, R*)]-5-(3-chlorophenyl)-3-[2-(3,4-dihydroxyphenyl)-1-methylethyl]-2-oxazolidinone which is an intermediate useful in making compounds that have antidiabetic and/or antihyperglycemic and/or anti-obesity properties in mammals.

2 Claims, No Drawings

PROCESS IMPROVEMENT IN THE SYNTHESIS OF [R-(R*,R*)]-1-5-(3-CHLOROPHENYL)-3-[2-(3,4-DIHYDROXYPHENYL)-1-METHYLETHYL]-2-OXAZOLIDINONE

This application is a continuation-in-part of application Ser. No. 08/164524 filed Dec. 9, 1993, allowed.

FIELD OF THE INVENTION

The invention is a process improvement for producing [R-(R*, R*)]-5-(3-chlorophenyl)-3-[2-(3,4-dihydroxyphenyl)-1-methylethyl]-2-oxazolidinone which is an intermediate useful in making compounds that have antidiabetic and/or antihyperglycemic and/or antiobesity properties in mammals.

BACKGROUND OF INVENTION

U.S. Pat. No. 5,061,727 teaches one method of making the desired oxazolidinone product. The oxazolidinone is isolated after an aqueous quench, extraction with an organic solvent, concentration, trituration with methyl alcohol and recrystallization in overall yield and 80-90% purity.

SUMMARY OF THE INVENTION

The invention is a one step process improvement for synthesizing a compound of Formula 1:

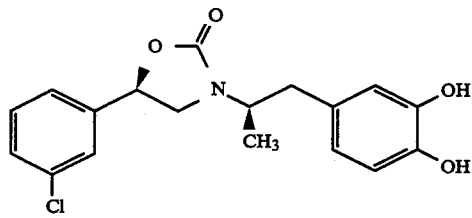

1 which comprises:

1.) reacting a compound of the formula:

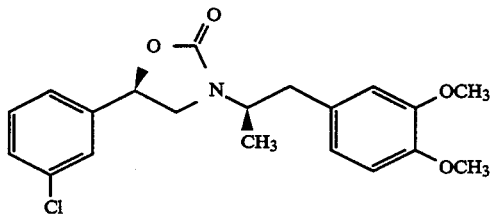

1 with boron tribromide in methylene chloride, under argon or nitrogen, at about −15° to +20° C., preferably −10° to 15° C. for 0.5–2 hours;

2.) quenching the reaction mixture, at about −5° to 10° C., preferably 0° to 10° C., with methyl alcohol;

3.) concentrating the reaction mixture, by distillation of methylene chloride;

4.) adding room temperature water to reaction;

5.) and collecting the precipitated crystalline product; of formula 1.

The advantages of this process over the cited literature are higher yields of product; higher purity of product; the elimination of a separate purification step; and the prevention of the formation of gummy solids, which are undesirable in kilogram scale reactions.

DETAILED DESCRIPTION OF THE INVENTION

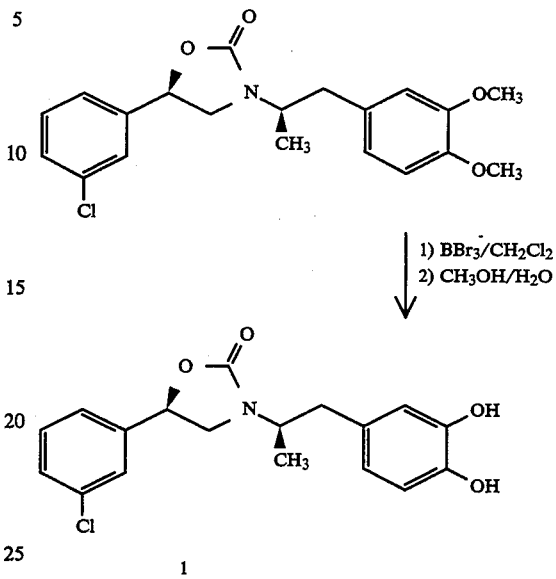

1

Referring to Scheme 1, [R-(R*,R*)]-5-(3-chlorophenyl)-3-[2-(3,4-dimethyloxyphenyl)-1-methylethyl]-2-oxazolidinone, obtained by literature procedures previously cited, is dissolved in methylene chloride, under argon or nitrogen at 0°–5° C. and boron tribromide is added, dropwise, to the reaction mixture. The progress of the reaction is monitored by thin layer chromatography or high pressure liquid chromatography. When the reaction is complete, it is quenched slowly with methyl alcohol at 0°–10° C., stirred at room temperature for 1–4 hours, and the excess solvent is removed by distillation. The mixture is cooled to room temperature. Water is added, dropwise, and the reaction mixture is stirred at room temperature for 2–72 hours. The resultant slurry is cooled to 5°–10° C. and stirred for 1.5 hours. The precipitate is collected, washed with water and dried to give the desired product, 1', in 88–94% yield and >95% wt/wt purity.

The advantages of this process over the cited literature are:

1.) higher yields of product (90 versus 75%);
2.) higher purities of product (>95 versus 80–90% wt/wt)
3.) the elimination of a separate purification step;
4.) and the prevention of the formation of gummy solids, which are undesirable in kilogram scale reactions.

This invention will be described in greater detail in conjunction with the following example.

EXAMPLE 1

[R-(R*,R*)]-5-(3-Chlorophenyl)-3-[2-(3,4-dihydroxyphenyl)-1-methylethyl]-2-oxazolidinone Twenty grams of [R-(R*,R*)]-5-(3-chlorophenyl)-3-[2-(3,4-dimethyloxyphenyl)-1-methylethyl]-2-oxazolidinone, prepared by the procedure described in U.S. Pat. No. 5,061,727, is dissolved in 100 ml of methylene chloride and cooled to 5° C. under a stream of argon. Ten ml of boron tribromide in 10 ml of methylene chloride is added dropwise over 25 minutes. The reaction mixture is stirred for 20 minutes at 0°–5° C. One hundred and fifty ml of methyl alcohol is added over 40 minutes and the reaction is allowed to warm to room temperature over 1 hour. The solvent is removed by distillation (pot temperature 90° C.) leaving an oil in the bottom of the flask. The reaction flask is charged with 36.9 g of methyl alcohol, cooled to room temperature and 148 g of water is added over 1.5 hours. The reaction is stirred at room temperature for 72 hours, followed by cooling to 5° C. and stirring at this temperature for 1 hour. The resulting precipitate is collected, rinsed with water, and dried to give 17.1 g of the desired product (Yield 92.7% theory).

LC Purity >95% wt/wt.

Calculated for $C_{18}H_{18}ClNO_4$: Theory: C=62.16; H=5.22; N=4.03; B=0.00; Br=0.00 Found: C=62.05; H=5.25; N=3.96; B=0.02; Br=0.36

$[\alpha]_D^{26} = -24\pm1$, C=1.1%

PILOT PLANT RUN

| Raw Materials: | |
|---|---|
| 9.9 kg | [R-(R*,R*)]-5-(3-chlorophenyl)-3-[2-(3,4-dimethyloxyphenyl)-1-methylethyl]-2-oxazolidinone |
| 69.0 kg | Methylene chloride |
| 14.0 kg | Boron tribromide |
| 59.0 kg | Methanol |
| 136.0 kg | Deionized water |

Equipment Set-up:
1 50 gallon kettle
1 100 gallon kettle
Distillation set-up between the kettles;
nitrogen purge valves;
Glycol to the condenser and jacket of 50 gallon kettle;
Water to the jacket of the 100 gallon kettle.

Procedure:

A 100% nitrogen purge rate is set up between the 2 kettles for 5 minutes, then the rate is reduced to 30-35%. Methylene chloride, 66.6 kg is charged into the 50 gallon kettle. Agitation at 75 RPM is started, 9.9 kg of [R-(R*,R*)]-5-(3-chlorophenyl)-3-[2-(3,4-dimethyloxyphenyl)-1-methylethyl]-2-oxazolidinone is added and the contents of the kettle are cooled to 0°-5° C. Boron tribromide, 14.0 kg, is charged into the reaction kettle at a set rate of 70 ml/min using a Cole-Parmer Teflon metering pump. The temperature is maintained at 0°-5° C. by adjusting the feed rate. After the completion of the addition, the nitrogen purge is stopped and the reaction is stirred for 60 minutes. The lines and metering pump are flushed out with 3 kg of methylene chloride. At the end of 1 hour, a 5 ml aliquot is taken to check the reaction progress. Thin layer chromatography indicates the completion of the reaction.

Methyl alcohol, 59-kg, is charged into the 50 gallon kettle over a period of 1 hour, while maintaining the temperature at 0°-10° C. by adjusting the flow rate of methyl alcohol. Distillation of the solvents is started by using hot water at about 50°-60° C. on the jacket of the 50 gallon kettle. Once the methylene chloride is removed, increase the jacket temperature to 70°-80° C. to distill the methyl alcohol. Distill until the volume is 30-35 liters collecting the distillate in the 100 gallon kettle. Cool the contents of the 50 gallon kettle to 20°-25° C. using water. Add 100 kg of deionized water to the 50 gallon kettle over a 2 hour period using a metering pump. Cool the batch to 0°-5° C. over 30-40 minutes using glycol on the jacket. Maintain the 0°-5° C. temperature overnight. Filter the batch on a 30 inch nutshell fitted with polypropylene cloth. Wash the cake twice with 18 kg of deionized water that has been cooled to 0°-5° C. Harvest the cake into poly-lined fiberglass trays and dry in a vacuum oven at 30°-35° C. until constant weight.

Yield 8,154 g (89.1% of theory), off white crystals.

LC Purity 96.2% wt/wt and 96.2% area.

Calculated for $C_{18}H_{18}ClNO_4C$: Theory: C=62.16; H=5.2; N=4.03; Cl=10.19; B=0.00; Br=0.00; Found: C=61.28; H=5.10; N=3.96; Cl=10.09; B=0.02; Br=1.42.

$[\alpha]_D^{26} = -24\pm1$, c=1.2%

$^1$H NMR (DMSO): δ 7.4-6.3 (m,7H); 5.50 (dd,5H,J=6.3 and 9.0Hz); 4.02 (m,1H); 3.89 (t,1H,J=9.1 Hz); 3.5-3.3 (bs,2H); 3.29 (dd,1H,J=6.3 and 9.0Hz); 2.6-2.4 (m,2H); 1.14 (d,3H,J=6.7 Hz).

$^{13}$CNMR(DMSO): δ 17.5, 39.5, 46.8, 49.8, 73.0, 115.5, 116.2, 119.6, 124.6, 126.1, 128.5, 129, 130.7, 133.4, 142.2, 143.8 145.2, 156.4.

IR(KBr): 3411, 2977, 1724, 1606 cm$^{-1}$.

We claim:

1. A process for making a compound of formula

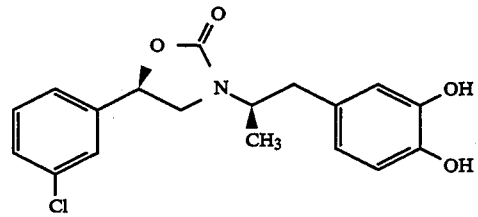

which comprises:

a) reacting, at about −15° to +20° C., [R(R*,R*)]-5-(3-chlorophenyl)-3-[2-(3,4-dimethyoxyphenyl)-1-methyl-ethyl]-2-oxazolidinone with boron tribromide in methylene chloride,,under argon for from 0.5 to 2 hours;

b) quenching the reaction mixture of about −5° to 10° C. with methyl alcohol;

c) concentrating the reaction mixture, by distillation of methylene chloride;

d) adding room temperature water to the reaction residue; and e) collecting the precipitated crystalline product of formula 1.

2. The process of claim 1 wherein the reaction temperature is about 0°-5° C. and the reaction mixture of about 0° to 10° C. is quenched.

* * * * *